(12) United States Patent
Hsiao

(10) Patent No.: US 7,584,671 B2
(45) Date of Patent: Sep. 8, 2009

(54) APPARATUS FOR TESTING THE LOAD BEARING STRENGTH OF AN ARCHITECTURAL STRUCTURE

(75) Inventor: Chiang-Pi Hsiao, Taipei (TW)

(73) Assignee: Architecture and Building Research Institute, Ministry of the Interior, Taipei (TW)

( * ) Notice: Subject to any disclaimer, the term of this patent is extended or adjusted under 35 U.S.C. 154(b) by 970 days.

(21) Appl. No.: 11/156,849

(22) Filed: Jun. 21, 2005

(65) Prior Publication Data
US 2006/0283261 A1 Dec. 21, 2006

(51) Int. Cl.
*G01N 3/02* (2006.01)
*G01N 3/10* (2006.01)

(52) U.S. Cl. .......................................... 73/856; 73/825
(58) Field of Classification Search .................... 73/760, 73/788, 790, 794, 804, 813, 816, 818, 819, 73/825, 856, 858
See application file for complete search history.

(56) References Cited

U.S. PATENT DOCUMENTS

| | | | | |
|---|---|---|---|---|
| 2,446,566 A * | 8/1948 | Wenk, Jr. ...................... | 73/795 |
| 3,423,994 A * | 1/1969 | Auksmann et al. ............ | 73/819 |
| 3,512,404 A * | 5/1970 | Jureit .......................... | 73/804 |
| 3,545,263 A * | 12/1970 | Kaye et al. ................... | 73/825 |
| 3,871,213 A * | 3/1975 | Jureit et al. .................... | 73/819 |
| 3,945,249 A * | 3/1976 | Knoth .......................... | 73/819 |
| 4,081,992 A * | 4/1978 | Aurora et al. ................... | 73/84 |
| 4,305,300 A * | 12/1981 | Petersen et al. ............... | 73/788 |
| 4,686,860 A * | 8/1987 | Liu .............................. | 73/856 |
| 4,843,888 A * | 7/1989 | Gram et al. .................... | 73/856 |
| 4,869,112 A * | 9/1989 | Gram et al. .................... | 73/856 |
| 5,138,887 A * | 8/1992 | Pohl ............................. | 73/856 |
| 5,379,645 A * | 1/1995 | Smart .......................... | 73/794 |
| 5,435,187 A * | 7/1995 | Ewy et al. ..................... | 73/856 |
| 5,448,168 A * | 9/1995 | Hirano et al. ................ | 324/209 |
| 5,633,467 A * | 5/1997 | Paulson ....................... | 73/800 |
| 5,777,236 A * | 7/1998 | Walls .......................... | 73/786 |
| 6,332,364 B1 * | 12/2001 | Buschmann et al. .......... | 73/788 |
| 6,729,189 B2 * | 5/2004 | Paakkinen .................... | 73/824 |
| 6,810,752 B1 * | 11/2004 | Yen ............................. | 73/855 |
| 2005/0011274 A1 * | 1/2005 | Ferguson et al. ............... | 73/818 |
| 2007/0051179 A1 * | 3/2007 | McMurtry et al. ............. | 73/760 |

FOREIGN PATENT DOCUMENTS

JP 62162940 * 7/1987

* cited by examiner

*Primary Examiner*—John Fitzgerald
(74) *Attorney, Agent, or Firm*—Davidson Berquist Jackson & Gowdey, LLP

(57) ABSTRACT

An apparatus for testing the load bearing strength of an architectural structure includes a top holding assembly, a hydraulic cylinder, a bottom holding assembly, and a bracing member. The hydraulic cylinder is disposed below the top holding assembly, and has a top end. The bottom holding assembly is mounted on the top end of the hydraulic cylinder, and cooperates with the top holding assembly to hold the architectural structure therebetween. The bottom holding assembly includes a peripheral wall. The bracing member has a plurality of bracing rollers disposed around and slidably abutting against the peripheral wall of the bottom holding assembly so as to absorb lateral horizontal stress which may occur during the testing of the architectural structure under compression.

7 Claims, 9 Drawing Sheets

APPARATUS FOR TESTING THE LOAD BEARING STRENGTH OF AN ARCHITECTURAL STRUCTURE

BACKGROUND OF THE INVENTION

1. Field of the Invention

The invention relates to an apparatus for testing the load bearing strength of an architectural structure, more particularly to an apparatus for testing the load bearing strength of an architectural structure in a fire simulating site.

2. Description of the Related Art

Referring to FIG. 1, a conventional apparatus for testing the load bearing strength of an architectural structure 11, such as a column, in a fire simulating site 1 is shown to include a bottom hydraulic cylinder 12, a bottom seat body 13 installed on the bottom hydraulic cylinder 12, a frame 14 disposed across and above the bottom seat body 13, a top hydraulic cylinder 15 installed on the frame 14, and a top seat body 16 installed on a bottom end of the top hydraulic cylinder 15 and corresponding to the bottom seat body 13. Additionally, the fire simulating site 1 is installed with sensor units and control units (not shown).

During testing, the architectural structure 11 is erected between the top and bottom seat bodies 16,13, and is subjected to stress by extending the top and bottom hydraulic cylinders 15,12 toward each other in an axial direction to simulate the stressing condition of the architectural structure 11 in an actual fire site. The environmental conditions of the fire simulating site 1 are then controlled for testing the load bearing strength of the architectural structure 11 during a fire.

Although the aforesaid prior art can be used to test the load bearing strength of the architectural structure 11 during simulated fire conditions, the architectural structure 11 may produce lateral horizontal stress at the top and bottom hydraulic cylinders 15,12 when the architectural structure 11 is not erected vertically or when the top and bottom seat bodies 16,13 are not aligned with each other, or when the architectural structure 11 is bent or deformed during the test. Specifically, the piston (not shown) in the bottom hydraulic cylinder 12 is stressed unevenly due to the lateral horizontal stress. Therefore, the bottom hydraulic cylinder 12 is easily damaged, and is thus required to be repaired or replaced frequently.

Furthermore, in a building structure, columns and beams are joined to each other. When the load bearing strength of a column-beam composite structure is tested using the aforesaid prior art, the apparatus of the prior art will be further subjected to the lateral horizontal stress from the beams, and is thus more easily damaged thereby.

SUMMARY OF THE INVENTION

The object of the present invention is to provide an apparatus for testing the load bearing strength of an architectural structure, which can absorb lateral horizontal stress occurring during the testing of the architectural structure under compression.

Therefore, the apparatus for testing the load bearing strength of an architectural structure according to this invention includes a top holding assembly, a hydraulic cylinder, a bottom holding assembly, and a bracing member. The hydraulic cylinder is disposed below the top holding assembly, and has a top end. The bottom holding assembly is mounted on the top end of the hydraulic cylinder, and cooperates with the top holding assembly to hold the architectural structure therebetween. The bottom holding assembly includes a peripheral wall. The bracing member has a plurality of bracing rollers disposed around and slidably abutting against the peripheral wall of the bottom holding assembly so as to absorb lateral horizontal stress which may occur during the testing of the architectural structure under compression.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
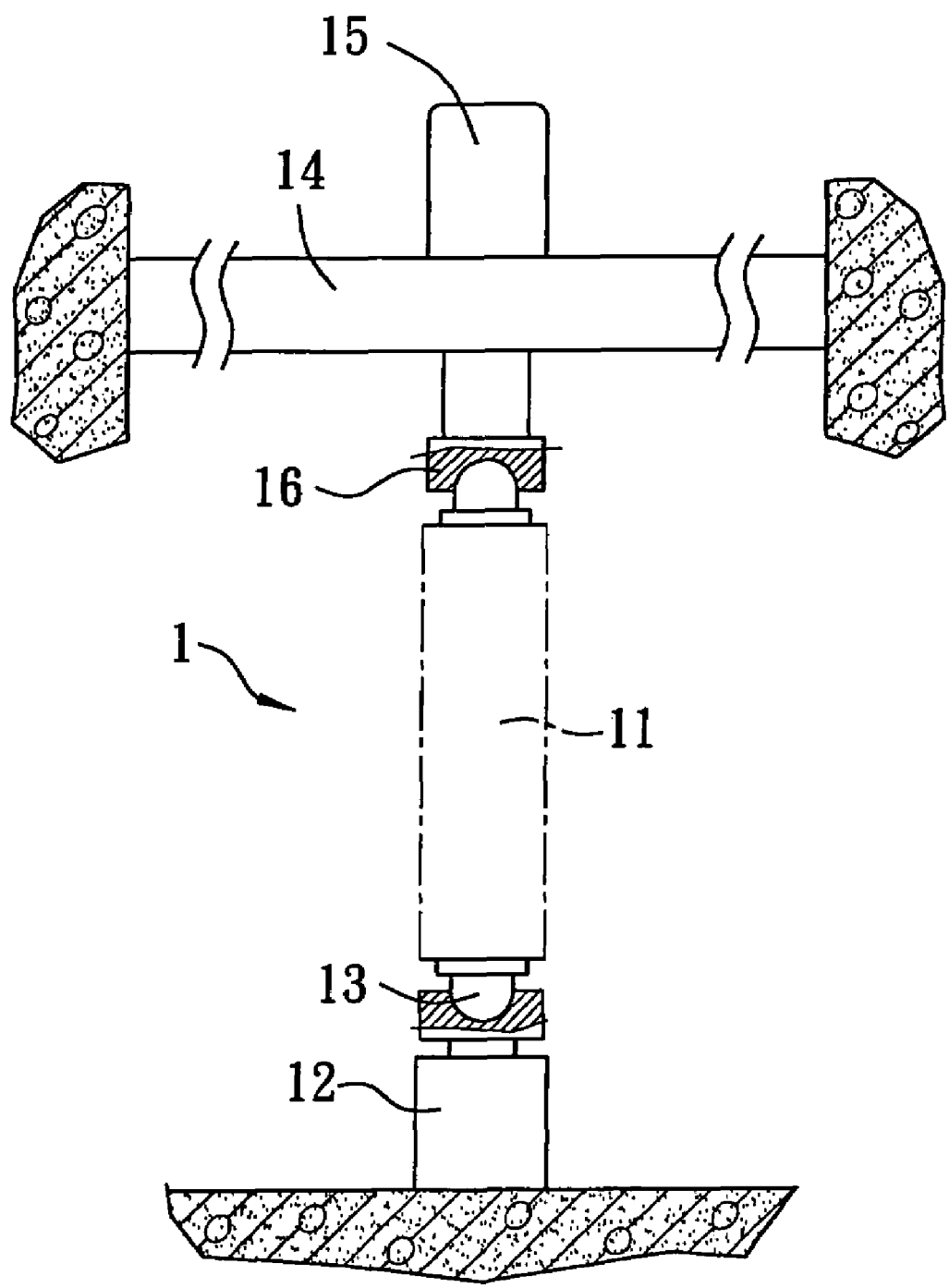
FIG. 1 is a fragmentary schematic view of a conventional apparatus for testing the load bearing strength of an architectural structure.
Figure 2:
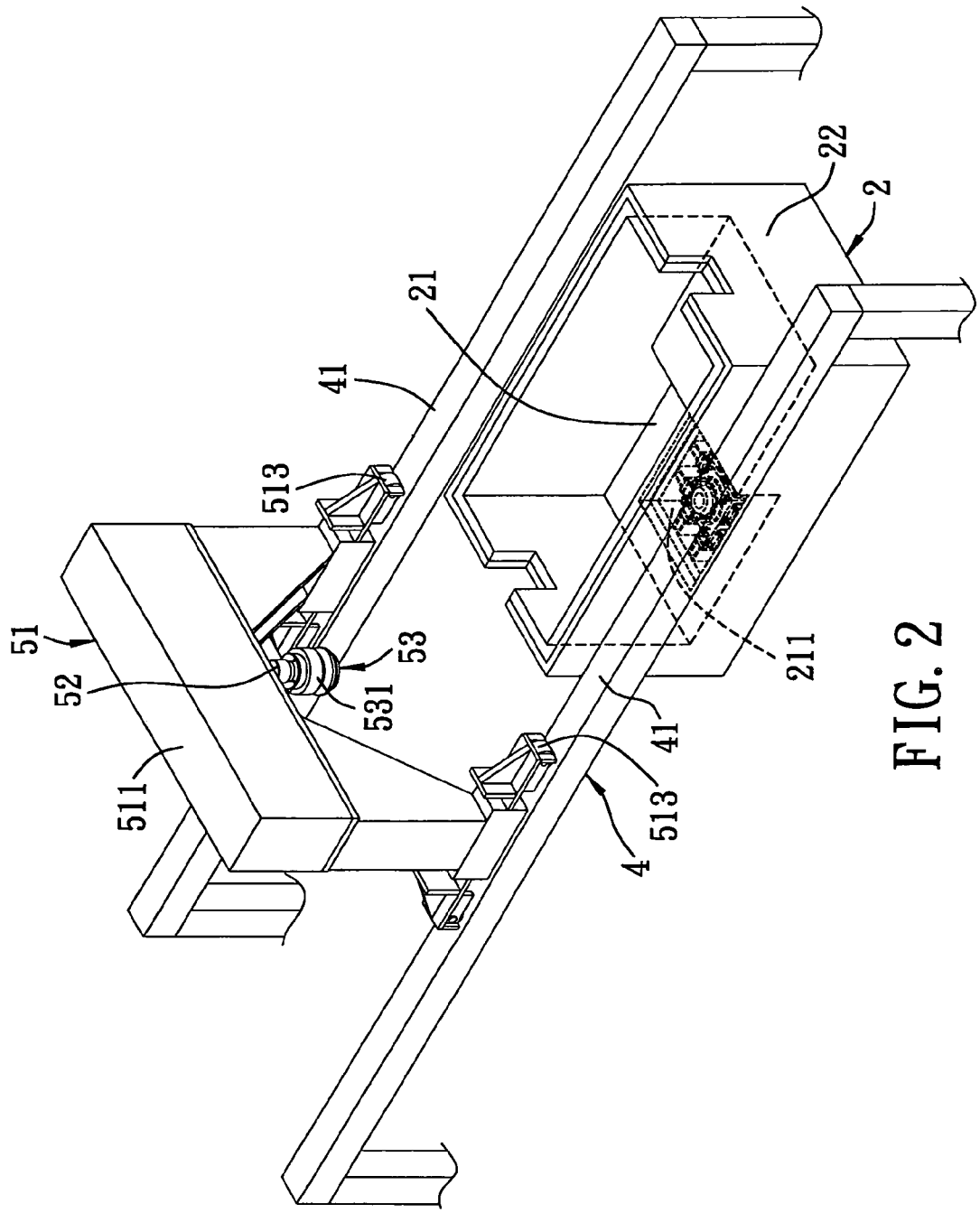
FIG. 2 is a perspective view of a preferred embodiment of the apparatus for testing the load bearing strength of an architectural structure according to this invention when installed in a fire simulating site.
Figure 3:
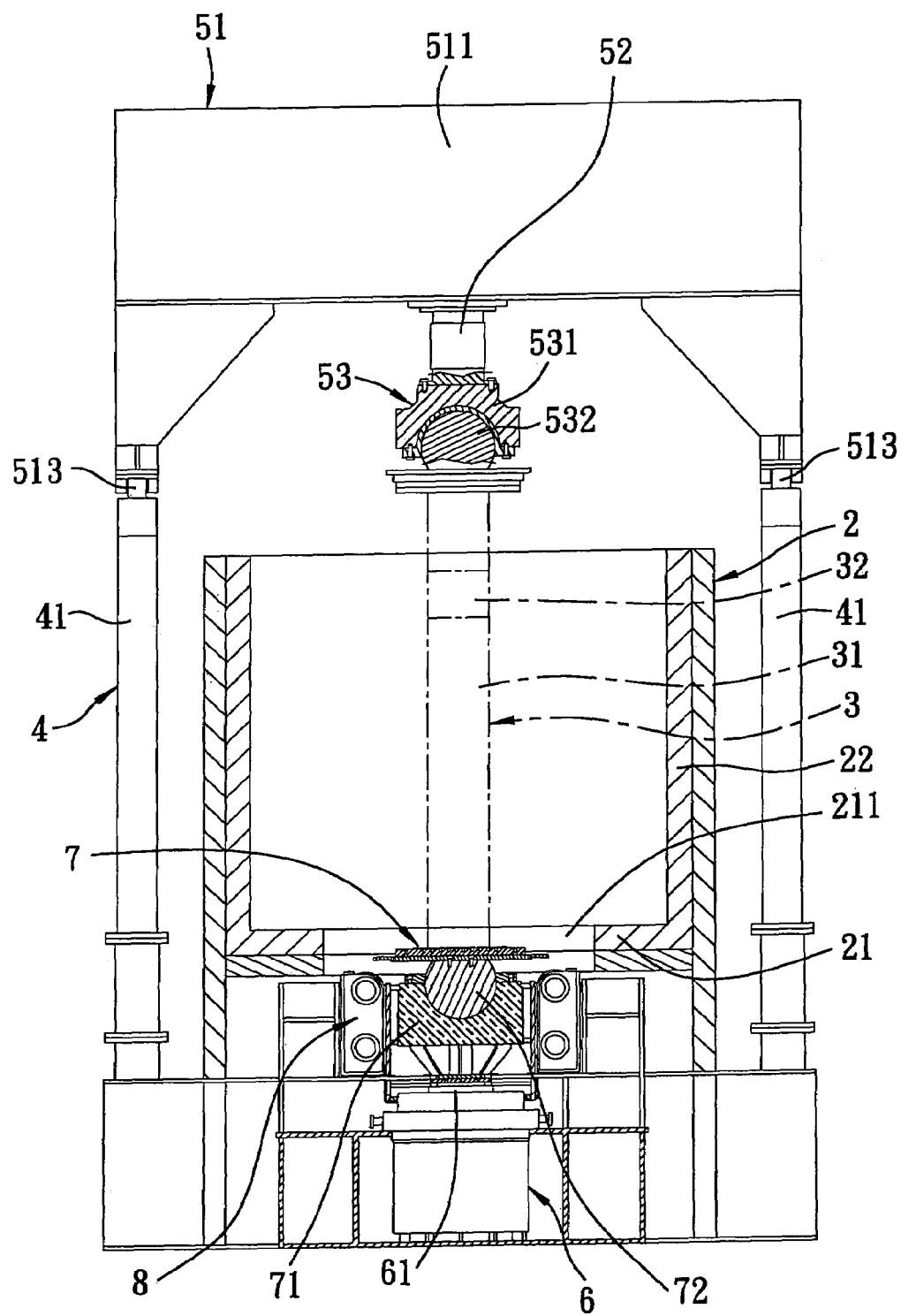
FIG. 3 is a sectional view of the preferred embodiment in an alignment state.
Figure 4:
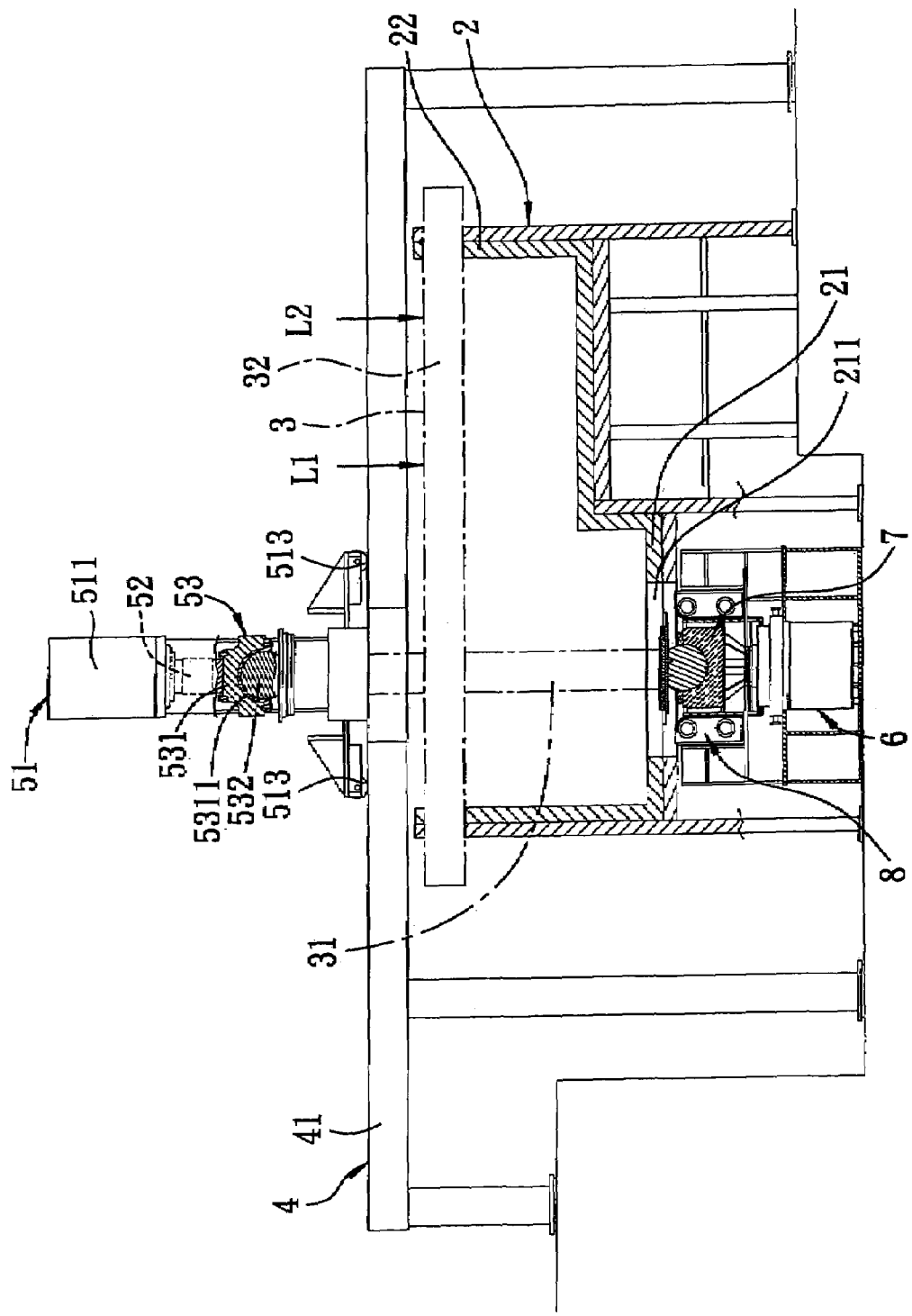
FIG. 4 is another sectional view of the preferred embodiment in the alignment state.
Figure 5:
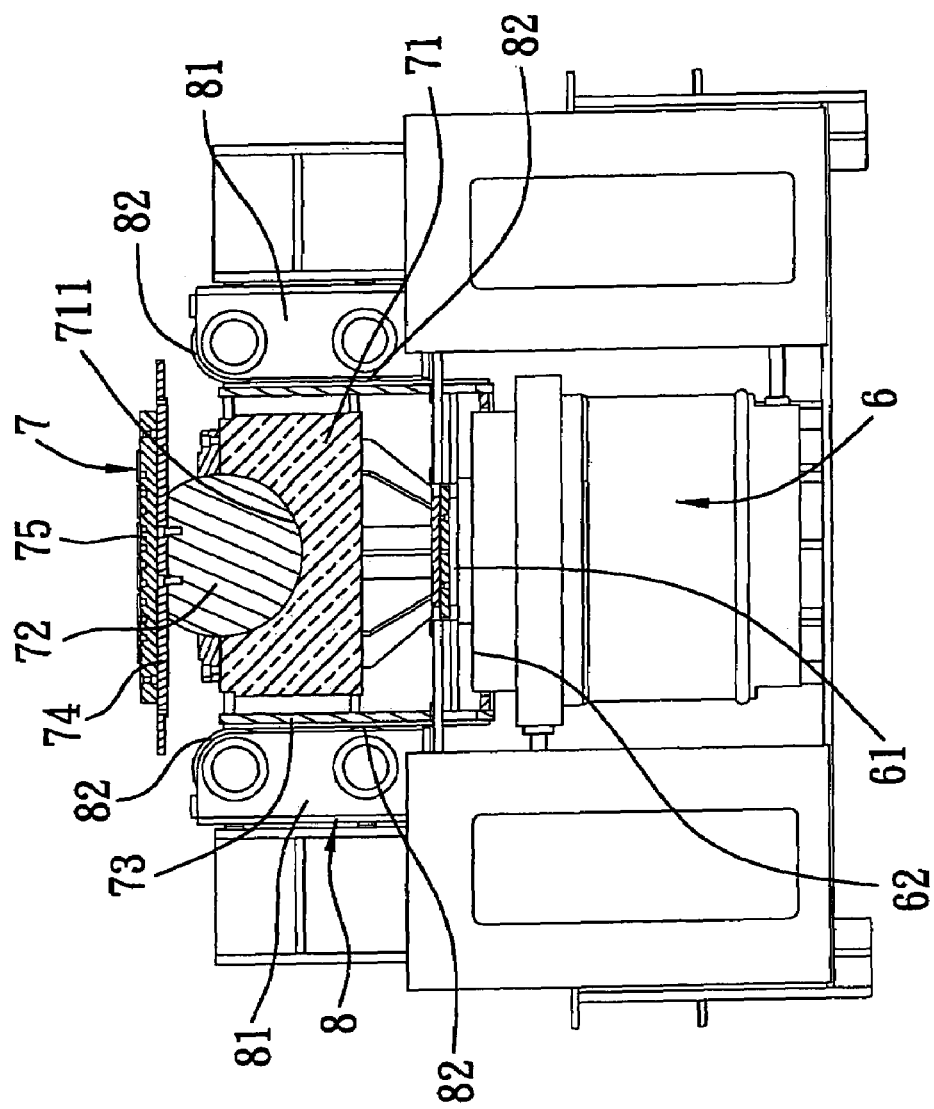
FIG. 5 is a fragmentary enlarged schematic sectional view of the preferred embodiment.
Figure 6:
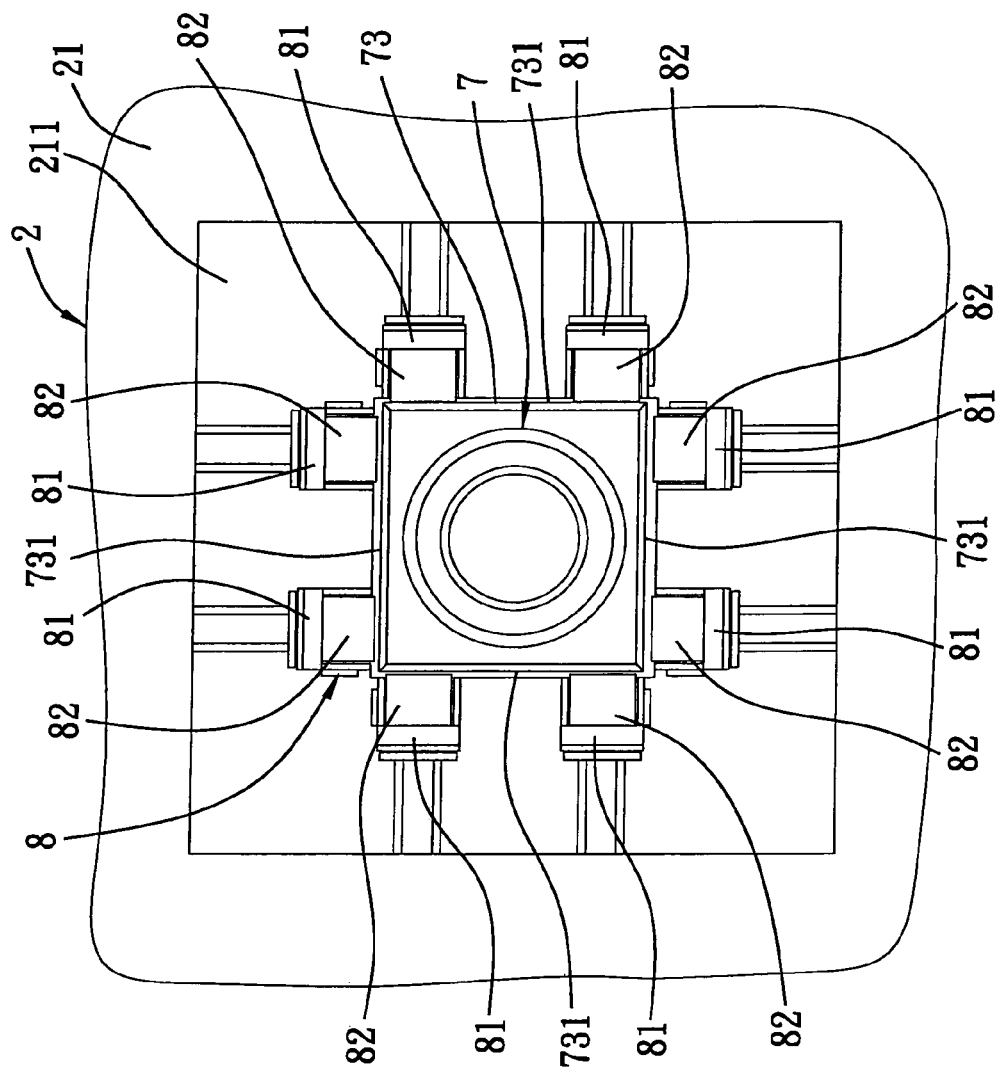
FIG. 6 is a fragmentary schematic top view of the preferred embodiment of FIG. 5.
Figure 7:
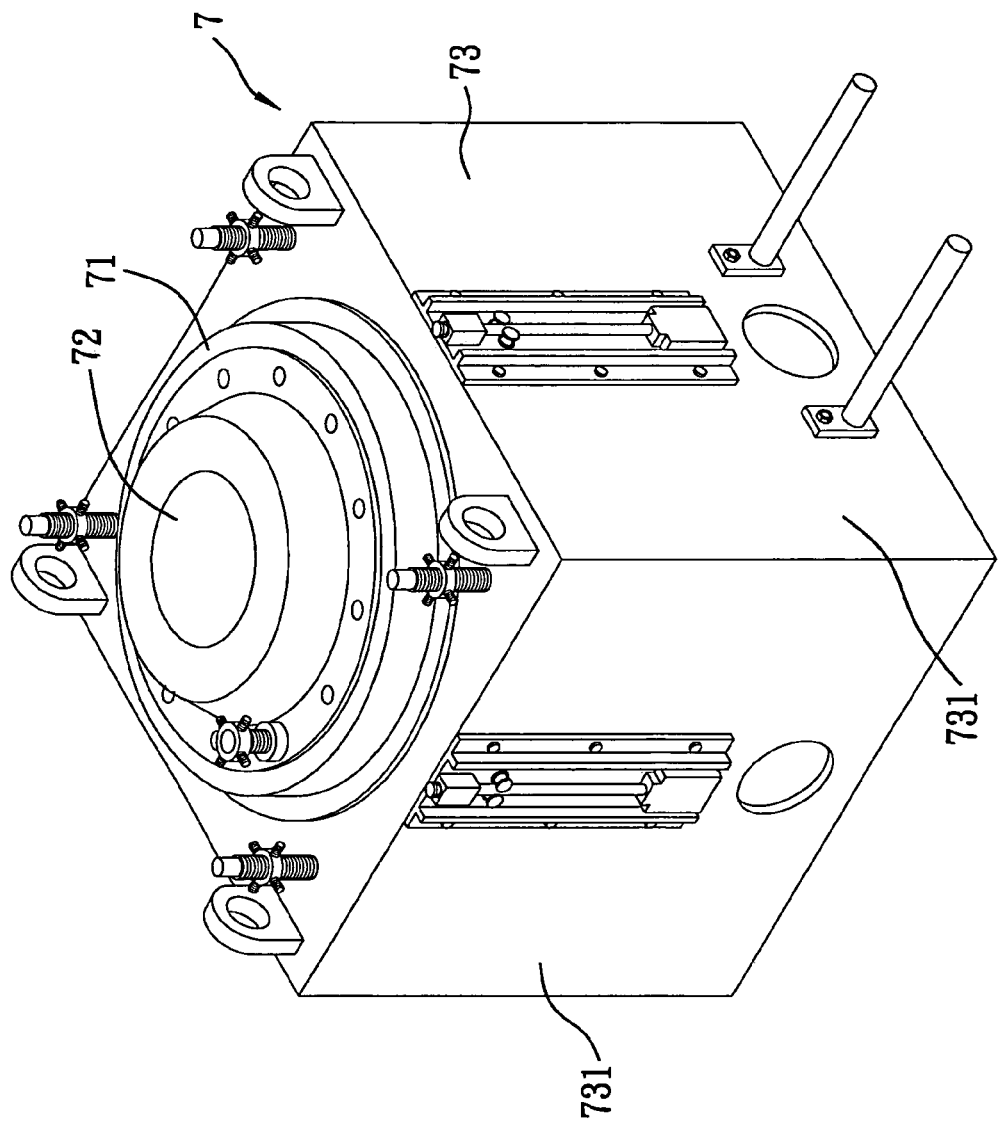
FIG. 7 is a perspective view of a bottom holding assembly of the preferred embodiment.
Figure 8:
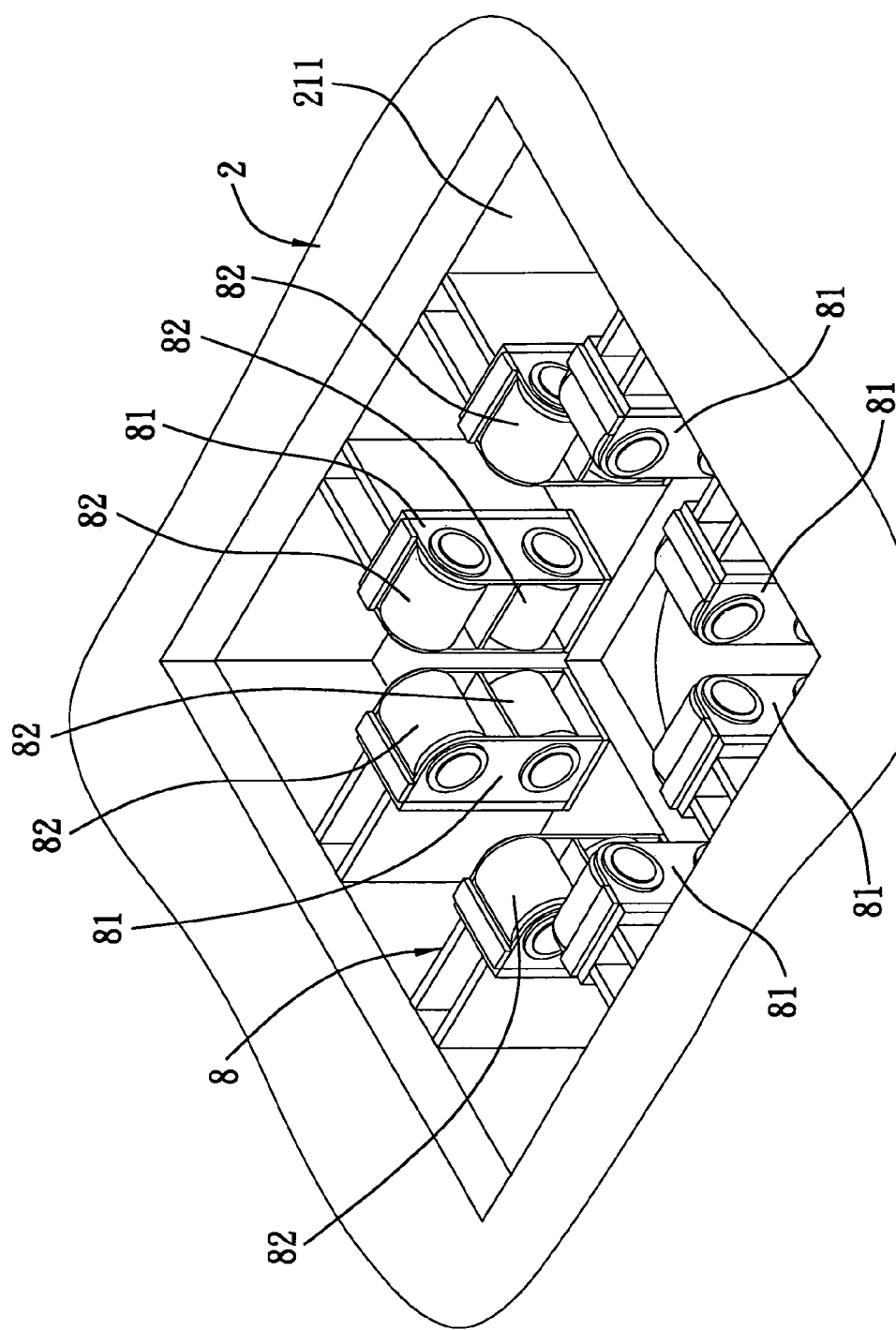
FIG. 8 is a perspective view of a bracing member of the preferred embodiment.

Referring to FIGS. 2, 3 and 4, the preferred embodiment of an apparatus for testing the load bearing strength of an architectural structure 3 according to this invention is shown to be installed in a fire simulating site 2. The fire simulating site 2 includes a bottom wall 21 having a through hole 211, and a peripheral wall 22 extending peripherally and upward from the bottom wall 21. The architectural structure 3 to be tested by the preferred embodiment is a column-beam composite structure having a column portion 31 and a beam portion 32 joined to the column potion 31. It should be noted that the preferred embodiment can also be used to test the load bearing strength of the architectural structure 3 that merely includes the column portion 31. The fire simulating site 2 can further include a top wall (not shown) capped on the peripheral wall 22. Additionally, the fire simulating site 2 includes a track unit 4, a main frame unit 51, and a top hydraulic cylinder 52. The track unit 4 includes a pair of rail elements 41 spaced apart from each other. The main frame unit 51 is mounted across the rail elements 41, and has a plurality of rollers 513 disposed slidably on the rail elements 41 for enabling the main frame unit 51 to slide along the rail elements 41 to a desired position. The top hydraulic cylinder 52 is mounted at a main cross bar 511 of the main frame unit 51.

Referring to FIGS. 4, 5, 6, 7, and 8, the preferred embodiment of the apparatus for testing the load bearing strength of the architectural structure 3 includes a top holding assembly 53, a bottom hydraulic cylinder 6, a bottom holding assembly 7, and a bracing member 8.

The top holding assembly 53 includes a top seat body 531 having a receiving recess 5311, and a top spherical body 532 corresponding to and slidably confined within the receiving recess 5311. The top holding assembly 53 is connected to the top hydraulic cylinder 52.

The bottom hydraulic cylinder 6 is disposed below the top holding assembly 53, under the fire simulating site 2, and corresponding to the through hole 211, and has a top end 62 and a plunger 61 extending upward at the top end 62.

The bottom holding assembly 7 is mounted on the top end 62 of the bottom hydraulic cylinder 6, and cooperates with the top holding assembly 53 to hold the architectural structure 3 therebetween. The bottom holding assembly 7 includes a seat body 71 supported on the plunger 61 of the bottom hydraulic cylinder 6 and having a receiving recess 711 on top thereof, a spherical body 72 corresponding to and slidably confined within the receiving recess 711, a peripheral wall 73 disposed on the top end 62 of the bottom hydraulic cylinder 6 and enclosing the seat body 71, a flat plate 74 mounted on the spherical body 72, and an insulating plate 75 mounted on the flat plate 74. The peripheral wall 73 of the bottom holding assembly 7 is rectangular, and has four side walls 731.

The bracing member 8 is disposed under the fire simulating site 2 corresponding to the through hole 211, and includes a plurality of bracing rollers 82 disposed around and slidably abutting against the peripheral wall 73 of the bottom holding assembly 7 so as to absorb lateral horizontal stress which may occur during the testing of the architectural structure 3 under compression. In the preferred embodiment, two pairs of the bracing rollers 82 are mounted adjacent to each of the four side walls 731 of the bottom holding assembly 7. It is noted that the number of the pairs of the bracing rollers 82 can vary according to the specific requirements in actual practice. The bracing member 8 further includes a plurality of roller seats 81 each of which carries one pair of the bracing rollers 82. Each pair of the bracing rollers 82 are spaced apart vertically. The peripheral wall 73 of the bottom holding assembly 7 is disposed between the seat body 71 of the bottom holding assembly 7 and the bracing rollers 82 of the bracing member 8.

Referring again to FIGS. 3, 4, and 5, during testing, the column portion 31 of the architectural structure 3 is erected on the insulating plate 75 of the bottom holding assembly 7. The top holding assembly 53 is slid to align with the bottom holding assembly 7, and the top spherical body 532 of the top holding assembly 53 is then disposed to abut against the top end of the column portion 31 of the architectural structure 3 so as to hold the architectural structure 3 between the top and bottom holding assemblies 53,7. The bottom hydraulic cylinder 6 is extended upwardly so as to compress the column portion 31 of the architectural structure 3, and the environmental conditions of the fire simulating site 2 are controlled for testing the load bearing strength of the architectural structure 3 under predetermined stress, temperature and duration conditions. The stress imposed on the architectural structure 3 is transmitted downwardly toward the bottom holding assembly 7. The lateral horizontal stress can be absorbed by the bracing member 8 so as to protect the bottom hydraulic cylinder 6 from damage due to lateral horizontal stress. Furthermore, the insulating plate 75 of the bottom holding assembly 7 provides an insulating effect for retarding heat transfer from the column portion 31 of the architectural structure 3 to the bottom holding assembly 7 and the bracing member 8. Therefore, service life and testing accuracy of the testing apparatus can be improved accordingly.

Figure 9:
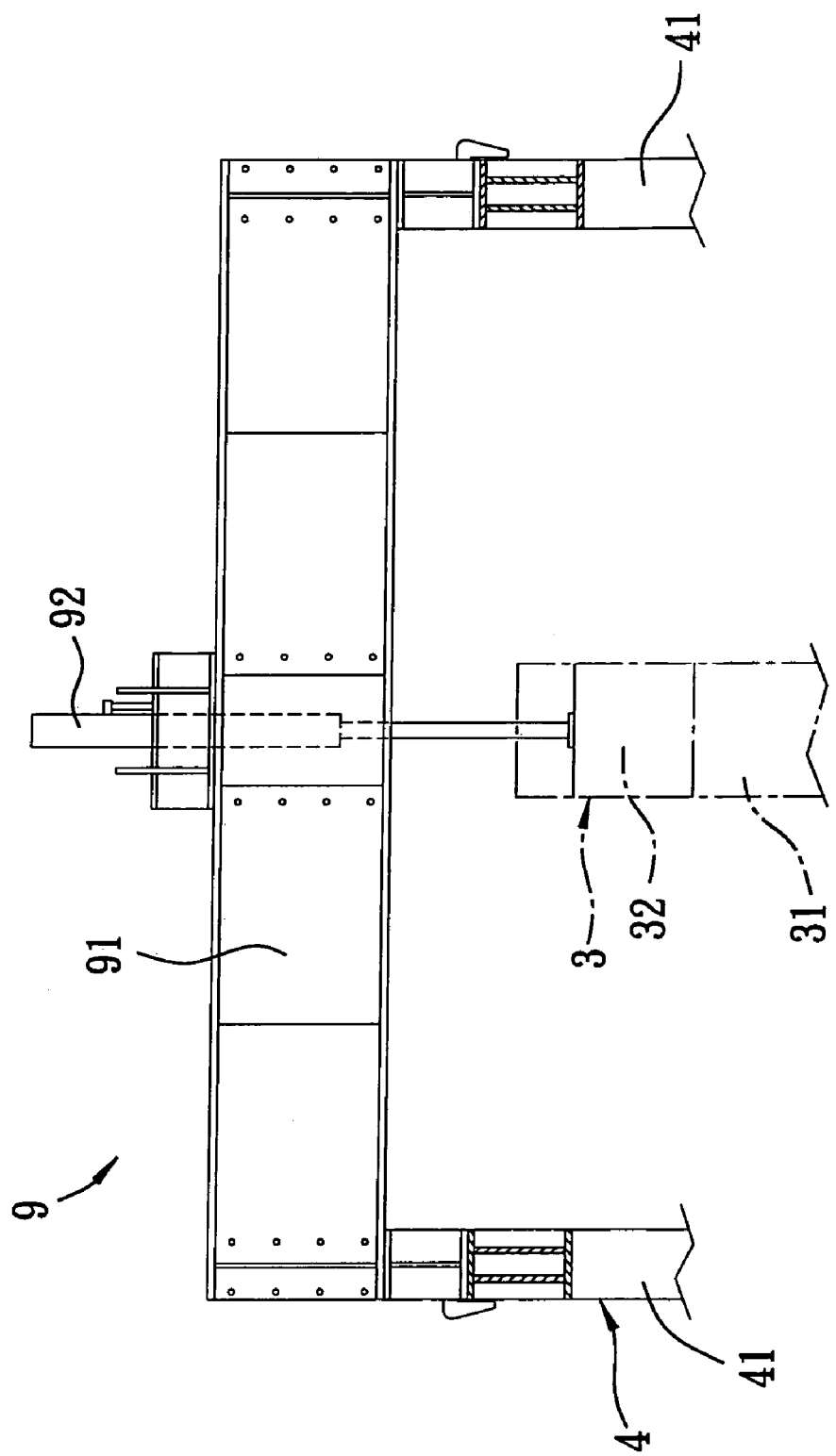
FIG. 9 is a fragmentary schematic view of a secondary frame unit of the preferred embodiment.

Referring to FIGS. 4 and 9, two secondary frame units 9 can be further used to impose loadings on the beam portion 32 of the architectural structure 3, as shown by arrows (L1,L2) in FIG. 4, so as to conduct a test for the composite load bearing strength of the architectural structure 3. In practice, the number of the secondary frame units 9 can be varied according to the specific requirements of the test. Each of the secondary frame units 9 includes a secondary cross bar 91 mounted across the rail elements 41, and a hydraulic cylinder 92 mounted on the secondary cross bar 91. The hydraulic cylinder 92 of each of the secondary frame units 9 is used to impose predetermined loading onto the beam portion 32 of the architectural structure 3. The lateral horizontal stress resulting from the loading imposed by the secondary frame units 9 on the beam portion 32 of the architectural structure 3 are further absorbed by the bracing member 8.

In view of the aforesaid, since the lateral horizontal stress occurring during the testing of the architectural structure 3 under compression can be absorbed by the bracing member 8, the damage drawback encountered in the prior art can be reduced. Furthermore, the bracing rollers 82 in each pair are spaced apart vertically so as to ensure the vertical bracing effect. Two pairs of the bracing rollers 82 are mounted adjacent to each of the four side walls 731 at two opposite edges, which further improves the effect for absorbing the lateral horizontal stress.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An apparatus for testing the load bearing strength of an architectural structure, comprising:
   a top holding assembly;
   a hydraulic cylinder disposed below said top holding assembly and having a top end;
   a bottom holding assembly mounted on said top end of said hydraulic cylinder and cooperating with said top holding assembly to hold the architectural structure therebetween, said bottom holding assembly including a peripheral wall; and
   a bracing member including a plurality of bracing rollers disposed around and slidably abutting against said peripheral wall of said bottom holding assembly so as to absorb lateral horizontal stress which may occur during the testing of the architectural structure under compression.

2. The apparatus as claimed in claim 1, wherein said peripheral wall of said bottom holding assembly is rectangular and has four side walls, two pairs of said bracing rollers being mounted adjacent to each of said four side walls of said bottom holding assembly, said bracing member further including a plurality of roller seats each of which carries one pair of said bracing rollers.

3. The apparatus as claimed in claim 2, wherein each pair of said bracing rollers are spaced apart vertically.

4. The apparatus as claimed in claim 1, wherein said bottom holding assembly includes a seat body having a receiving recess on top thereof and a spherical body corresponding to and slidably confined within said receiving recess, said peripheral wall of said bottom holding assembly being disposed between said seat body and said bracing rollers of said bracing member.

5. The apparatus as claimed in claim 4, wherein said hydraulic cylinder includes a plunger extending upward at said top end of said hydraulic cylinder to support said seat body of said bottom holding assembly.

6. The apparatus as claimed in claim 4, wherein said bottom holding assembly further includes a flat plate mounted on said spherical body, and an insulating plate mounted on said flat plate.

7. An apparatus for testing the load bearing strength of an architectural structure in a fire simulating site where a top end of the architectural structure is to be held by a top holding assembly, the apparatus comprising:

a bottom holding assembly adapted to hold a bottom end of the architectural structure and including a peripheral wall;

a hydraulic cylinder having a top end supporting said bottom holding assembly; and a bracing member including a plurality of bracing rollers disposed around and slidably abutting against said peripheral wall of said bottom holding assembly so as to absorb lateral horizontal stress which may occur during the testing of the architectural structure under compression.

\* \* \* \* \*